(12) United States Patent
Kaus et al.

(10) Patent No.: US 9,014,466 B2
(45) Date of Patent: Apr. 21, 2015

(54) REGION-COMPETITIVE DEFORMABLE MESH ADAPTATION

(75) Inventors: Michael Kaus, Hamburg (DE); Todd R. McNutt, Verona, WI (US); Vladimir Pekar, Hamburg (DE); Matthias Meyer, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1536 days.

(21) Appl. No.: 11/573,290

(22) PCT Filed: Jul. 28, 2005

(86) PCT No.: PCT/IB2005/052552
§ 371 (c)(1),
(2), (4) Date: Feb. 6, 2007

(87) PCT Pub. No.: WO2006/016317
PCT Pub. Date: Feb. 16, 2006

(65) Prior Publication Data
US 2007/0211939 A1 Sep. 13, 2007

Related U.S. Application Data

(60) Provisional application No. 60/599,904, filed on Aug. 9, 2004.

(51) Int. Cl.
*G06K 9/00* (2006.01)
*G06T 7/00* (2006.01)
*A61B 6/00* (2006.01)
*G06K 9/62* (2006.01)
*G06T 17/20* (2006.01)

(52) U.S. Cl.
CPC ............... *G06T 7/0083* (2013.01); *A61B 6/00* (2013.01); *G06K 9/6209* (2013.01); *G06T 7/0081* (2013.01); *G06T 7/0089* (2013.01); *G06T 17/20* (2013.01); *G06T 17/205* (2013.01); *G06T 2207/10081* (2013.01); *G06T 2207/20116* (2013.01); *G06T 2207/30008* (2013.01); *G06T 2207/30028* (2013.01)

(58) Field of Classification Search
USPC .................................................. 382/128–132
See application file for complete search history.

(56) References Cited

U.S. PATENT DOCUMENTS

| | | | |
|---|---|---|---|
| 5,859,891 | A | 1/1999 | Hibbard |
| 6,735,277 | B2 | 5/2004 | McNutt et al. |
| 7,010,164 | B2 | 3/2006 | Weese et al. |

FOREIGN PATENT DOCUMENTS

WO   2004010374 A2   1/2004

OTHER PUBLICATIONS

Of Timinger et al "Integration of interactive correction to model based segmentation algorithms" Proc. Bildverabietung fuer die medizin Nov. 15, 2003.*

(Continued)

*Primary Examiner* — Sean Motsinger

(57) ABSTRACT

An image segmentation method segments a plurality of image features in an image. The plurality of image features are segmented non-simultaneously in succession. The segmenting of each image feature includes adapting an initial mesh to boundaries of the image feature. The segmenting of each image feature further includes preventing the adapted mesh from overlapping any previously adapted mesh.

11 Claims, 8 Drawing Sheets

(56) References Cited

OTHER PUBLICATIONS

Camara, O., et al.; Computational modeling of thoracic and abdominal anatomy using spatial relationships for image segmentation; 2004; Real-Time Imaging; 10:263-273.

Colliot, O., et al.; Description of brain internal structures by means of spatial relations for MR image segmentation; 2004; Proc. of SPIE Medical Imaging; vol. 5370; pp. 444-454.

Fletcher, P.T., et al.; Deformable M-Rep Segmentation of Object Complexes; 2002; IEEE; pp. 26-29.

Kaus, M.R., et al.; Automated 3-D PDM Construction from Segmented Images Using Deformable Models; 2003; IEEE Trans. on Med. Imaging; 22(8)1005-1013.

McInerney, T., et al.; Deformable organisms for automatic medical image analysis; 2002; Medical Image Analysis; 6:251-266.

Pekar, V., et al.; Automated Model-Based Organ Delineation for Radiotherapy Planning in Prostatic Region; 2004; Int. J. Radiation Oncology Biol. Phys.; 60(3)973-980.

Pitiot, A., et al.; Expert Knowledge Guided Segmentation System for Brain MRI; 2003; LNCS; vol. 2879; pp. 644-652.

Rosenfeld, A., et al.; Sequential Operations in Digital Picture Processing; 1966; J. of Assoc. for Computing Machinery; 13(4)471-494.

\* cited by examiner

REGION-COMPETITIVE DEFORMABLE MESH ADAPTATION

CROSS REFERENCE TO RELATED APPLICATIONS

This application claims the benefit of U.S. provisional application Ser. No. 60/599,904 filed Aug. 9, 2004, which is incorporated herein by reference.

The following relates to the image processing arts. It finds particular application in the segmenting or contouring of planning images in conjunction with development of a treatment plan for radiation therapy, and will be described with particular reference thereto. However, it finds application in image segmentation and contouring generally, and in methods and systems employing image segmentation and contouring, such as diagnostic medical imaging, magnetic resonance angiography, and so forth.

In performing radiation therapy, a tomographic radiation beam, or a plurality of radiation beams, are intensity-modulated using multileaved collimators or other beam-shaping elements to precisely irradiate the cancerous region while limiting radiation exposure of sensitive nearby organs at risk. The radiation therapy session or sessions are planned prior to radiation treatment based on one or more planning images of the radiotherapy subject acquired by computed tomography or another imaging technique. In a usual approach, the cancerous tumor and nearby organs at risk are identified within the planning image using image segmentation. Each item of interest (tumor, organ, or so forth) is segmented using a three-dimensional contour or mesh to identify spatial boundaries of the tumor or organ. Intensity modulation parameters are optimized to deliver radiation primarily within contours or meshes corresponding to cancerous regions (tumors, cancer-ridden organs, or so forth) while limiting radiation exposure within contours or meshes corresponding to organs at risk.

Manual segmenting or contouring of the planning image is labor-intensive. Each surface is in general a stack of two-dimensional boundaries that must be fitted to the boundaries of the corresponding tumor or organ by stretching, shifting, or otherwise manipulating small portions of the surface until the entire three-dimensional surface conforms with the organ or other item being contoured. This process is repeated for each image slice of each cancerous region and for each organ at risk. Errors in contouring can lead to inadequate irradiation of the cancer, radiation damage of surrounding organs, or both.

In view of these difficulties and concerns, automation of part or all of the contouring process is desirable. In some automated contouring methods, the three-dimensional surface is divided into a polygonal mesh. For example, triangular mesh elements can be employed, and coordinates of the vertices of the triangular mesh elements are iteratively adjusted until the mesh surface substantially corresponds with boundaries of the contoured region. The optimization of the mesh employs optimization criteria incorporating figures of merit such as: (i) finding one or more image features in each polygonal mesh element; (ii) minimizing an energy parameter trading off image feature points and the shape of the mesh; and so forth.

Usually, more than one item of interest is segmented. For example, in a prostate cancer treatment, the cancer-ridden prostate is contoured as the target of radiation therapy, while the bladder, rectum, and femur heads are contoured as organs of risk whose radiation exposure is to be limited. Because these organs are close to one another, the computer-optimized contours or meshes may overlap. Such overlap is problematic, particularly if the contour of an organ at risk such as the bladder or rectum overlaps with the contour of a targeted organ such as the prostate. In such cases, the status of the overlapping region is ambiguous: Should radiation be targeted into the overlap region as part of the targeted organ, or should the overlap region be avoided as part of an organ at risk?

In one approach for avoiding contour or mesh overlaps, a "spring" aspect is introduced into each mesh component. As two contours come together during the optimization, the spring aspect prevents the contours from crossing and overlapping. Such approaches have certain difficulties, however. First, they may fail if the contours overlap initially, for example if contours provided by the user or by an automated contour initiation algorithm overlap. Indeed, the spring aspect in such cases may prevent the erroneous initial overlap from being corrected during optimization.

Second, a high strength for the spring aspect can introduce an inaccurately large separation between neighboring meshes. This can be problematic if boundaries of the organs represented by the meshes are in fact close to one another (or perhaps even pressing against one another), such that their respective meshes should have closely proximate or coinciding surfaces in the contact region. Conversely, if the spring aspect is set to a lower strength, it may be inadequate to avoid overlapping of meshes.

The following contemplates improved apparatuses and methods that overcome the aforementioned limitations and others.

According to one aspect, an image segmentation method is provided for segmenting a plurality of image features in an image. The plurality of image features are segmented non-simultaneously in succession. The segmenting of each image feature includes adapting an initial mesh to boundaries of the image feature. The segmenting of each image feature further includes preventing the adapted mesh from overlapping any previously adapted mesh.

According to another aspect, an image segmentation apparatus is disclosed for segmenting a plurality of image features in an image. A means is provided for segmenting the plurality of image features non-simultaneously in succession. The segmenting of each image feature includes adapting an initial mesh to boundaries of the image feature. The segmenting of each image feature further includes preventing the adapted mesh from overlapping any previously adapted mesh.

One advantage resides in automated contouring or segmenting having improved robustness.

Another advantage resides in avoiding contour overlaps in the contouring or segmentation solutions.

Another advantage resides in improved contouring accuracy.

Yet another advantage resides in improved workflow efficiency in the segmentation process.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a radiation therapy system for performing a radiation therapy treatment.

FIG. 2 diagrammatically shows the contouring processor of the radiation therapy system of FIG. 1.

Figure 1:
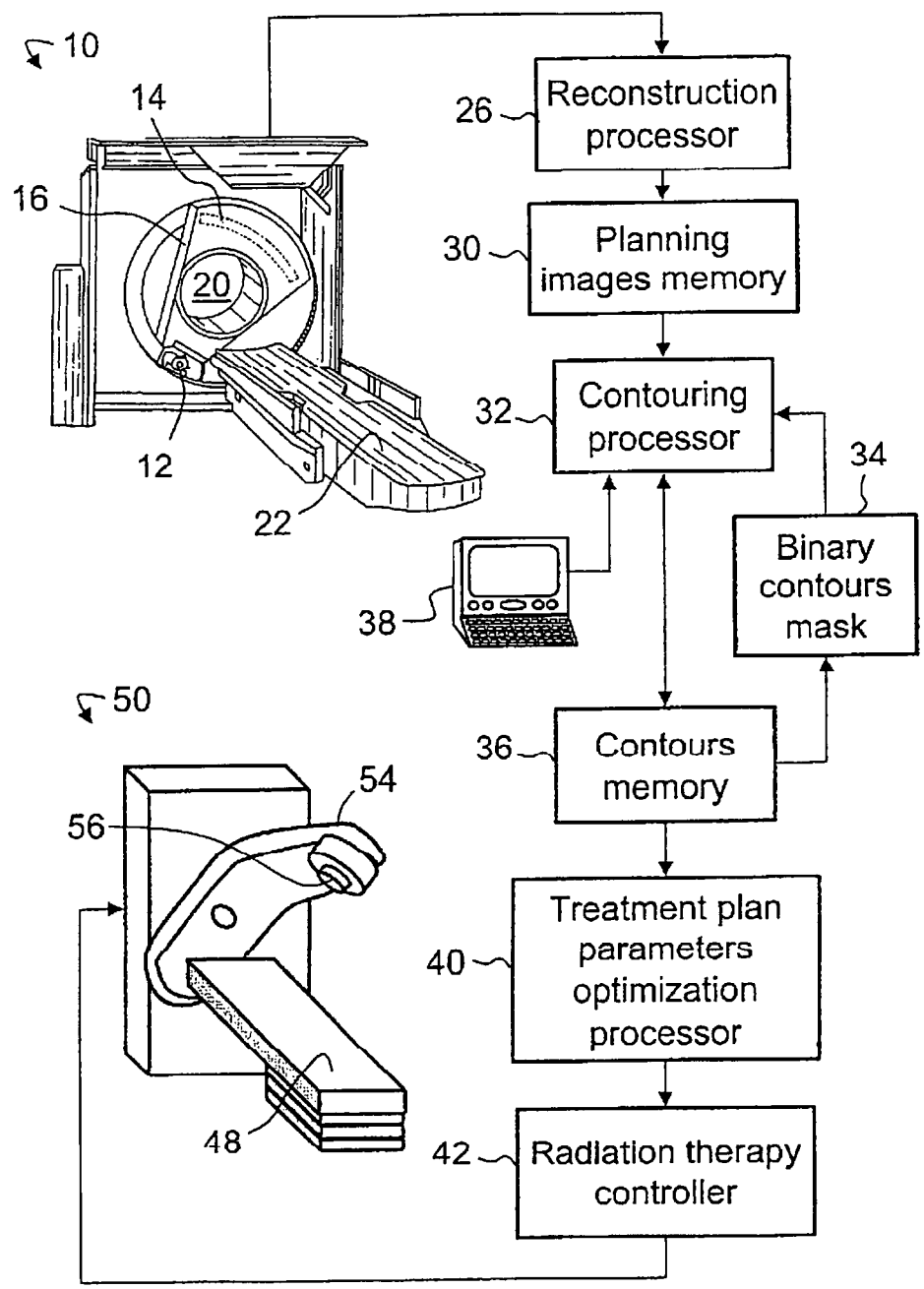

With reference to FIG. 1, a radiation therapy system includes a planning computed tomography imaging scanner 10. The illustrated scanner 10 includes a cone-beam x-ray source 12 and a two-dimensional x-ray detector array 14 mounted on a rotating gantry 16 on opposite sides of an imaging region 20. (The x-ray source 12, detector array 14, and rotating gantry 16 are exposed in FIG. 1 for expository purposes; however, it will be appreciated that typically these components are enclosed in a stationary gantry housing). A radiation therapy subject, such as a cancer patient (not shown), is disposed on a patient support 22 and moved into the imaging region 20, and computed tomography projection data of the subject are acquired using the scanner 10. A reconstruction processor 26 employs filtered backprojection or another image reconstruction algorithm to reconstruct the acquired projection data into one or more planning images of the radiation therapy subject. The reconstructed planning images are stored in a planning images memory 30.

A contouring processor 32 defines and fits a three-dimensional surface contour to the planning image of the tumor or other malignant tissue to be irradiated and, typically, also contours of one or more organs at risk in the planning image. For example, in the case of a patient with prostate cancer, the cancerous prostate is contoured, and nearby organs at risk of receiving excessive radiation exposure during the radiation therapy are also contoured. In the case of prostate radiation therapy, such organs at risk may include, for example, the rectum and the bladder. The contouring processor 32 optionally includes a manual graphical user interface through which a radiation technician manually defines the contours using a pointer or other control. The contouring processor optimizes each mesh or contour with respect to its corresponding tumor, organ at risk, or other target. As each contour is optimized by stretching, shifting, or otherwise moving portions of the mesh or contour, it is checked against other contours using a binary contours mask 34 that indicates excluded voxels contained by other contours. The voxels contained by other contours are excluded voxels in the sense that these voxels are excluded from also being included in the contour currently being optimized. This ensures that the contour currently being optimized does not overlap other contours.

The resulting one or more contours are stored in a contours memory 36. Other anatomical data derived from the one or more planning images are also typically stored in the contours memory 36, such as radiation attenuation or tissue density information. The contours optimization can proceed automatically using a suitable mesh or contour optimization algorithm, or can be performed manually through a graphical user interface 38. If automated contour optimization is used, then the graphical user interface 38 enables the user to verify the contour fitting and, if needed, further enables the user to correct or fine-tune the automatically fitted contours.

The anatomical information stored in the contours memory 36 is used by a radiation treatment plan parameters optimization processor 40 to determine optimized parameters for the radiation treatment plan. In intensity modulated radiation therapy, a plurality of radiation beams, or a single radiation beam tomographically revolved around the subject, are used to irradiate the tumor or other malignant tissue. The optimization processor 40 optimizes parameters such as: multileaved collimator settings that define the aperture shape; global beam intensity or weight; beam direction; wedge angle; fractionation schedule; and so forth using optimization criteria including at least: (i) producing substantial irradiation of the malignant tissue; and (ii) limiting irradiation of the organs at risk. The optimized treatment plan parameters are stored in a treatment plan parameters memory 42.

As a quantitative example of radiation therapy parameters optimization, if there are nine discrete angular beam positions arranged at 40° intervals around the subject and each beam position has a 10×10 $cm^2$ beam area selectively divided into 0.5×0.5 $cm^2$ beamlets by a multileaved collimator, then there are 9×400=3600 beamlets to be optimized. Each of the nine radiation beams can also have global parameters such as overall beam intensity or weight, beam direction, wedge angle, fractionation schedule, and so forth. One optimization technique suitable for optimizing this large number of parameters is disclosed in McNutt et al., U.S. Pat. No. 6,735,277 (WO 03/099380).

At the radiation therapy session, the subject is placed on a movable table or other subject support 48 of a radiation delivery system 50. Typically, the subject, or at least that portion of the subject which is to receive radiation therapy, is substantially immobilized on the subject support 48 using straps, clamps, cushions or other body restraints. In the illustrated embodiment, the radiation delivery system 50 is a tomographic system that includes a linear electron accelerator (i.e., linac) 54 producing an accelerated electron beam impinging upon a tungsten or other target to generate a beam of x-rays or gamma rays for irradiating the subject. A multileaved collimator 56 shapes or intensity modulates the x-ray or gamma ray beam. The radiation source is tomographically revolved about the subject during treatment to irradiate the subject over a range of angular views up to 360°. Instead of the illustrated tomographic radiation delivery system 50, other radiation delivery systems can be used, such as a multiple beam system in which a plurality of radiation sources are angularly spaced at fixed or adjustable angular positions around the subject gantry and produce multiple radiation beams that simultaneously or alternately irradiate the subject. For example, nine radiation sources, each having a separate multileaved collimator, can be arranged at 40° intervals around the subject to provide the nine beam positions of the previous quantitative parameters optimization example.

Figure 2:
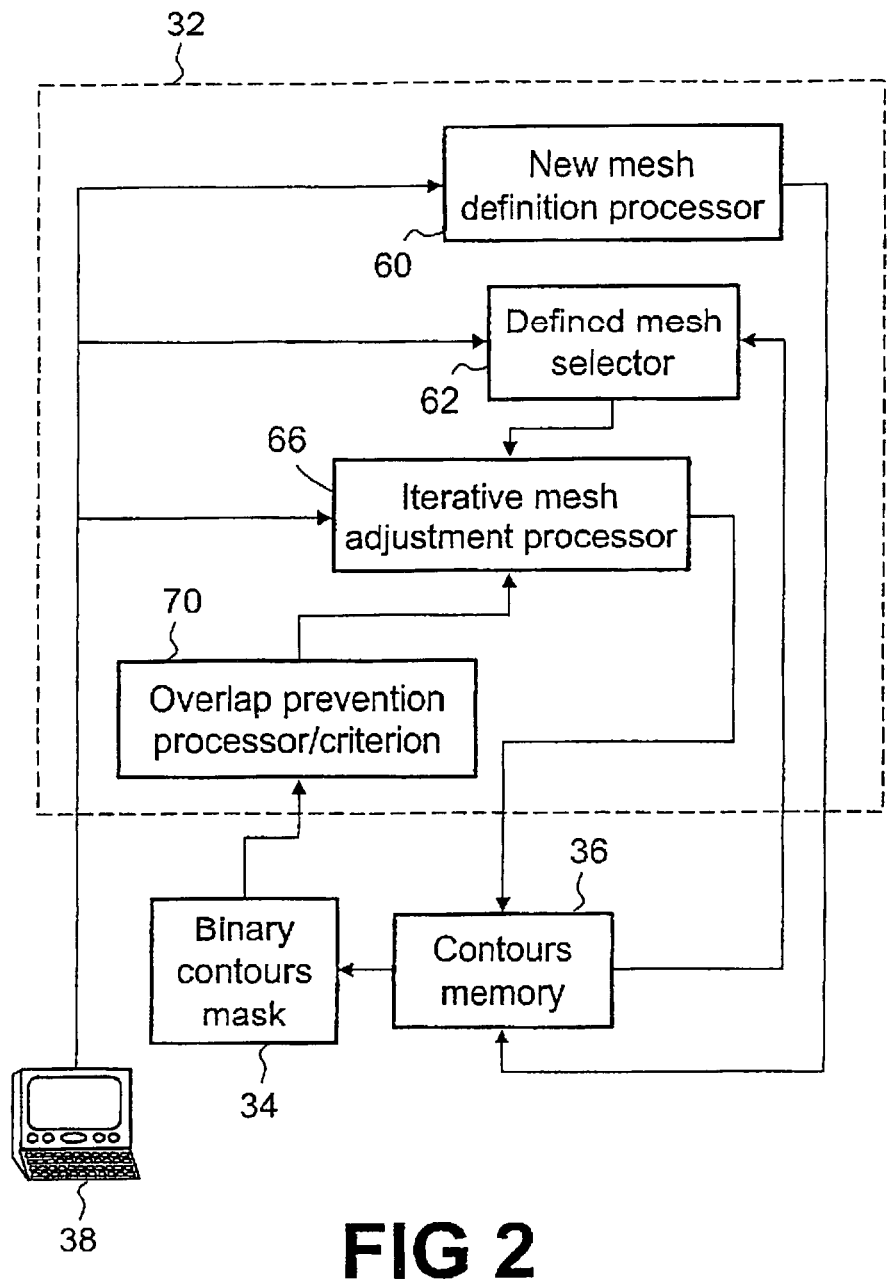

With reference to FIG. 2, a suitable example embodiment of the contouring processor 32 is described. A new mesh definition processor 60 defines a new mesh. In the illustrated embodiment, this is done through the user interface 38; for example, the user can employ a pointing device to identify a center of an image feature of interest. In other embodiments, the new mesh definition processor 60 defines meshes automatically, for example using a pattern recognition algorithm to identify features of interest. The newly defined mesh, which is not yet optimized with respect to boundaries of the corresponding image feature of interest, is stored in the meshes memory 36. In a similar manner, any number of meshes can be defined.

A defined mesh selector 62 is used to identify a current mesh for adjustment. Only one mesh can be adjusted at any given time. The selection can be made by the user via the user interface 38, or selection can be automatic. Preferably, the selector 62 selects defined meshes for adjustment in the sequence from easiest to define accurately to hardest. For example, in transmission computed tomography imaging, bone has a significantly distinct contrast from adjacent soft tissue, has a well-defined shape, remains relatively stationary during imaging, and so is a good candidate to optimize first. An iterative mesh adjustment processor 66 performs iterative adjustment of the mesh or contour to adapt the mesh or contour to the boundaries of the corresponding image feature of interest. The adjustment iterations can be manual—the user inputs successive selected adjustments to user-selected portions of the mesh via the user interface 38. Alternatively or additionally, automated iterative adjustment can be performed based on a suitable iterative optimization algorithm.

During iterative adjustment of the selected contour, an overlap prevention processor/criterion 70 is operative to prevent the defined mesh or contour currently being adjusted from overlapping other defined meshes or contours. The overlap prevention processor/criterion 70 references the binary contours mask 34 to identify pixels or voxels of the image which are contained in contours other than the defined contour currently being adjusted. The binary mask 34 has a map of binary bits having a bit-to-pixel or bit-to-voxel correspondence with the image. A bit having a first binary value (for example, binary "1") indicates that the corresponding voxel or pixel is an excluded voxel or pixel which is excluded from the mesh or contour currently being fitted because it is contained by one of the other meshes or contours. A bit having a second binary value (for example, binary "0") indicates that the corresponding voxel or pixel is not contained by any other defined contour, and hence is available for incorporation into the current defined mesh being adjusted.

In one approach, the overlap prevention processor/criterion 70 performs an overlap check after each adjustment iteration. The overlap check determines whether the adjusted mesh or contour overlaps any other mesh or contour. This check is readily performed with reference to the binary mask 34—an overlap is indicated by the current mesh or Contour under adjustment containing one or more voxels whose corresponding bits in the binary mask 34 indicate the voxels are excluded voxels. If an overlap is found, then the overlap prevention processor/criterion 70 adjusts the current mesh or contour to remove the overlap. An alternative way of checking if a triangle of a second mesh is inside a first mesh is to count the number of intersections along the triangle normal. If the number of intersections is even, then the triangle is not inside the mesh.

In another approach, the overlap prevention processor/criterion 70 provides an adjustment selection criterion that is incorporated into an iterative criteria-based optimization performed by the iterative mesh adjustment processor 66. The adjustment selection criterion provided by the overlap prevention processor/criterion 70 ensures that excluded bits are not selected for inclusion into the current mesh or contour by the adjustment iteration. For example, the adjustment selection criteria may produce a selection value for each voxel under consideration between 0 and 255, with 0 indicating that the voxel is not part of the feature of interest being contoured and 255 strongly biasing toward incorporation of the voxel. For such criteria, the adjustment selection criterion provided by the overlap prevention processor/criterion 70 should set to 0 the value for any voxel indicated as excluded in the binary mask 34. Alternatively, the criteria can be iteratively adjusted until the overlapping portion of the current mesh moves outside of the masked area.

Although only the one mesh or contour currently selected by the selector 62 can be adjusted at any given time, in some embodiments the optimization of one mesh is not necessarily completed before beginning adjustment of another mesh. That is, for example, a first defined mesh could be partially adjusted and optimized, followed by selection of a second defined mesh which is partially adjusted and optimized, followed by re-selection of the first defined mesh for further optimization. In such a back-and-forth approach, the currently selected mesh should be "deleted" from the binary mask 34 when it is selected for adjustment by setting the bits corresponding to the selected mesh to the binary value not indicating exclusion. Once the current mask is de-selected by the selector 62, it is "put back" into the binary mask 34 by setting the bits corresponding to the de-selected mesh to the binary value indicating exclusion.

In other embodiments, each mesh is optimized in succession, and once a mesh is optimized is no longer adjustable. In such embodiments, the current mesh is not entered into the binary mask 34 until its adjustment is completed, at which time the current mesh is de-selected and the corresponding bits are assigned exclusion binary values in the binary mask 34.

Figure 3A:
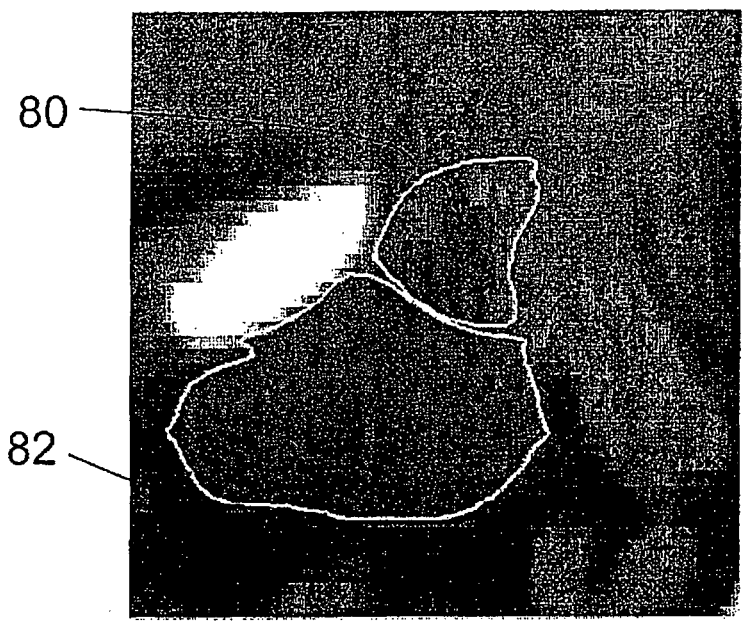
FIG. 3A shows an example image with two existing defined contours.
Figure 3B:
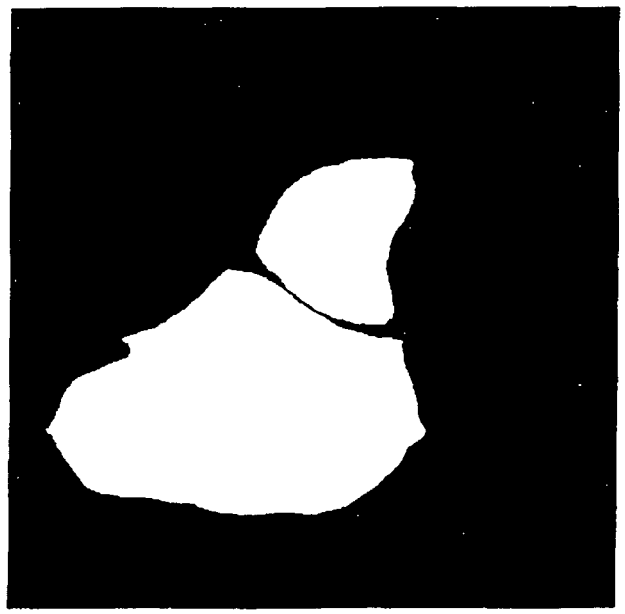
FIG. 3B shows a binary contours mask corresponding to the image with two existing defined contours of FIG. 3A.

With reference to FIGS. 3A and 3B, the use of a binary mask to identify excluded voxels is illustrated for a specific example image. FIG. 3A shows the example image, along with two adjusted meshes or contours 80, 82 corresponding in the illustrated example to the bladder and prostate organs. FIG. 3B shows the corresponding binary mask, in which excluded pixels contained by one of the existing defined contours 80, 82 are white while pixels not contained by any existing defined contour are black pixels.

Figure 4A:
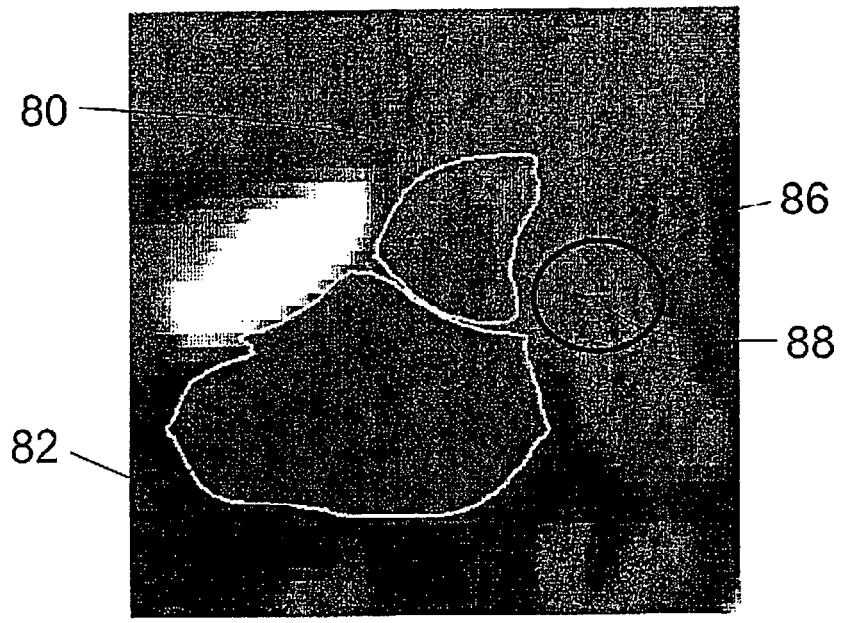
FIG. 4A shows the image with two existing defined contours of FIG. 3A with an initial contour selected by a user employing an on-screen cursor.
Figure 4B:
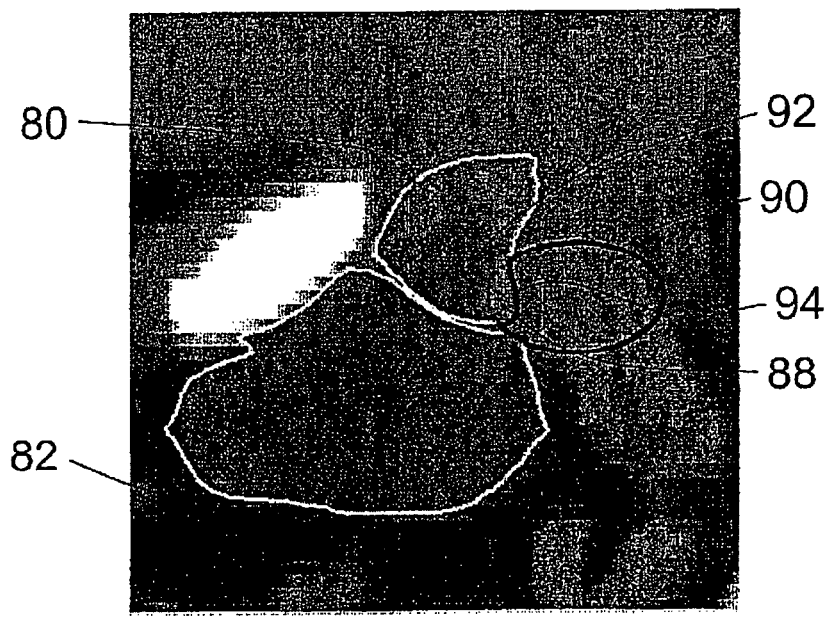
FIG. 4B shows a user-performed adjustment of the contour of FIG. 4A, in which the overlap prevention processor of the contouring processor prevented the user-performed adjustment from overlapping the existing defined contours.

With reference to FIGS. 4A and 4B, contour overlap protection in the context of a manual adjustment of a current mesh or contour is illustrated. An initial contour 86 is shown in FIG. 4A, and is to be used for contouring the rectum. The initial contour 86 is a default circular contour positioned, for example, around a position indicated by the user via an on-screen cursor 88 of a pointing device. FIG. 4B shows an adjustment iteration performed by the user by moving the on-screen cursor 88 to the left, into the existing defined contour 80. The resulting updated contour 90 would include a portion 92 (indicated by a dotted curve) overlapping the existing defined contour 80. However, the overlap prevention processor 70 detects the overlap using the binary mask of FIG. 3B, and adjusts the portion 92 to define a corrected portion 94 of the updated contour 90 which properly lies outside of the other existing contours 80, 82. While the example of FIGS. 4A and 4B pertain to user adjustment of initial contour 86, the illustrated overlap prevention processing is also operative at other times during contour adjustment, such as when the user adjusts an automatically fitted contour to correct for an error in the automated fitting, or when an automatic fitting process tries to expand into a region of excluded voxels.

Figure 5:
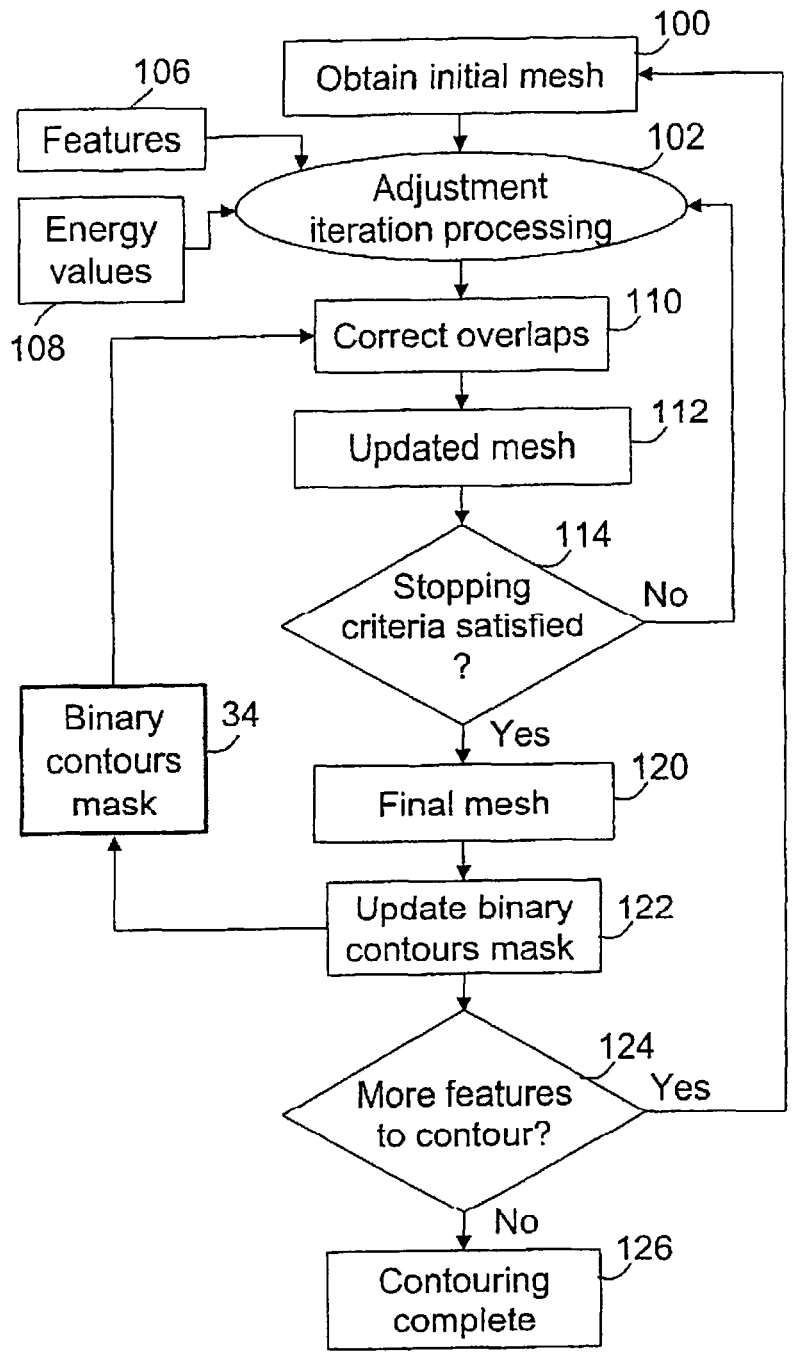
FIG. 5 shows a process flow diagram for an automatic contouring process performed by the contouring processor of FIG. 2.

With reference to FIG. 5, an automated contours optimization suitably performed by the contouring processor 32 is described. An initial contour is obtained by the new mesh definition processor 60 in process operation 100. The initial contour can be user selected or determined using pattern recognition or another automatic algorithm. An adjustment iteration is performed by the iterative mesh adjustment processor 66 in process operation 102. The adjustment iteration can employ substantially any type of criteria for selecting deformation of the contour. In some embodiments, a polygonal mesh is employed as the contour, made up for example of triangle mesh components in which neighboring triangles having abutting sides and common vertices. Coordinates of vertices of the triangle mesh components are adjusted based on adjustment selection criteria such as an image features criterion 106 and an energy value criterion 108. For example, the image features criterion 106 characterizes the extent of image features incorporated by the prospective adjustment, while the energy value criterion 108 characterizes the "strain energy" imposed upon the mesh by the prospective adjustment.

After the adjustment, the overlap prevention processor 70 checks the adjusted polygonal mesh against the binary contours mask 34 and corrects any overlaps with other contours in process operation 110, producing an updated contour 112 resulting from the adjustment iteration. At a decision process operation 114, it is decided whether or not the polygonal mesh optimization should be terminated. The decision 114 uses suitable stopping criteria such as integrated percentage change in mesh component positions, maximum mesh component adjustment, or so forth. If further iterating is indicated, process flow passes back to the adjustment iteration process operation 102. When optimization is complete, the resulting contour is the final contour 120. The binary mask 34 is updated in process operation 122 by setting voxels contained by the final contour 120 to the exclusion binary value. At a decision process operation 124, it is decided whether or not there are more features to contour. If so, then process control passes to the initial contour process operation 100; if not, then control terminates at the contouring complete process operation 126.

Figure 6:
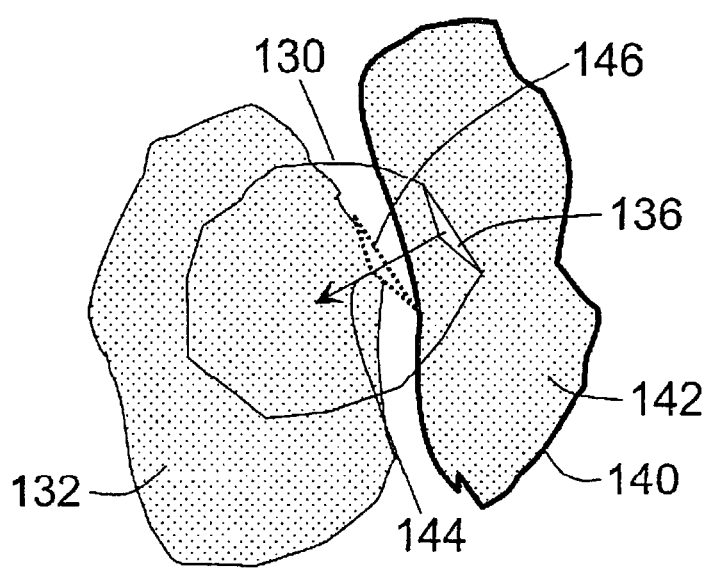
FIG. 6 illustrates a suitable method for correcting an adjustment that produces an overlap of the current contour with an already optimized contour.

FIG. 6 illustrates a suitable overlap correction performed by the overlap prevention processor 70. In the example of FIG. 6, a polygonal mesh 130 is being adjusted to adapt it to boundaries of an image feature 132. After an adjustment iteration, a triangular polygonal mesh component 136 lies within an existing mesh 140 already fitted to an image feature 142. The overlap prevention processor 70 detects the overlap using the binary mask 34. The detected overlap is corrected by shifting the vertices of the triangular polygonal mesh component 136 along a direction to new vertex positions 146 (indicated by dotted lines in FIG. 6) that lie outside of the already optimized mesh 140. The shift direction vector is calculated as the mean vector of all triangle edge vectors of one mesh that intersect a triangle of the other mesh. The new vertex positions are calculated by finding the closest point of intersection with the second mesh along the shift direction vector.

The automated contours optimization process flow illustrated in FIG. 5 advantageously avoids overlaps of meshes or contours. It will be appreciated that even if the initial contour selected in the process operation 100 overlaps a previously optimized contour, such initial overlapping will be removed during the overlaps correction process operation 110 in the first adjustment iteration.

Figure 7:
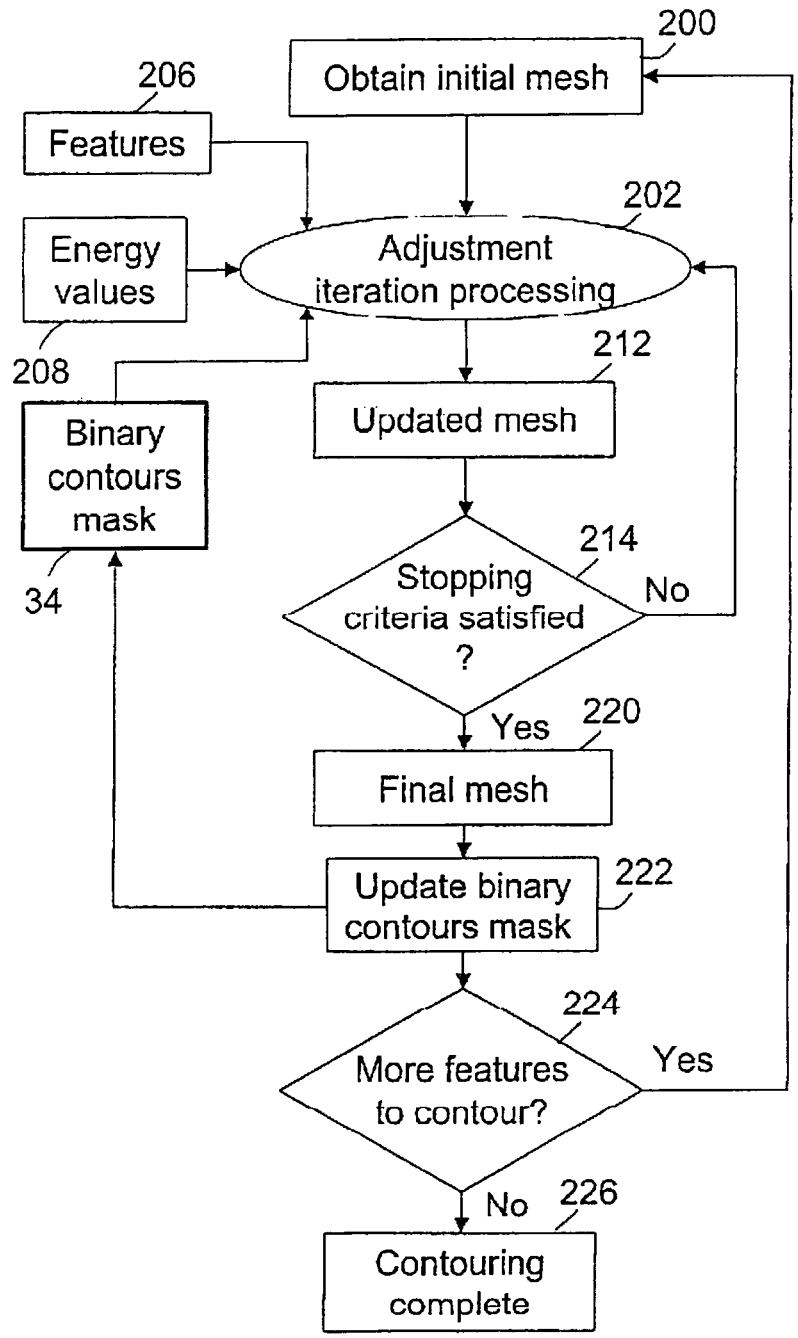
FIG. 7 shows another process flow diagram for an automatic contouring process suitably performed by the contouring processor of FIG. 2.

With reference to FIG. 7, another automated contours optimization suitably performed by the contouring processor 32 is described. An initial contour is obtained by the new mesh definition processor 60 in process operation 200. The initial contour can be user selected or chosen automatically. An adjustment iteration is performed in process operation 202. The adjustment iteration can employ substantially any type of criteria for selecting deformation of the contour, such as a image features criterion 106 and a energy value criterion 108. Additionally, the adjustment iteration process operation 102 employs an overlap prevention criterion derived from the binary contours mask 34 by the overlaps prevention processor 70. The overlap prevention criterion value assigned to excluded voxels is such that the adjustment iteration process operation will not adjust the contour to include such excluded voxels. Accordingly, the iterative adjustment never produces overlaps, and the output of the adjustment iteration process operation is an updated contour 212 which does not overlap any previously fitted contour. (In contrast, the automated contours optimization of FIG. 5 may produce an overlap which, however, is always removed by the overlaps correction process operation 110).

At a decision process operation 214, it is decided whether or not the polygonal mesh optimization should be terminated. The decision 214 uses suitable stopping criteria. If further iterating is indicated, process flow passes back to the adjustment iteration process operation 202. When optimization is complete, the resulting contour is the final contour 220. The binary mask 34 is updated in process operation 222 by setting voxels contained by the final contour 220 to the exclusion binary value. At a decision process operation 224, it is decided whether or not there are more features to contour. If so, then process control passes to the initial contour process operation 200; if not, then control terminates at the contouring complete process operation 226.

When using either the contours optimization process flow illustrated in FIG. 5 or the contours optimization process flow illustrated in FIG. 7, it is advantageous to start contouring using the most well-defined features. For example, in transmission computed tomography images the most well-defined features are typically those features having the highest radiation attenuation; thus, hard features, such as bone, are usually more well-defined than soft features in transmission computed tomography images. Hence, for these images the bone structures should generally be fitted first, followed by less well-defined structures. For other imaging modalities that have different contrast characteristics, features other than bone may be the most well-defined features, and hence the features which should be fitted first.

Figure 8A:
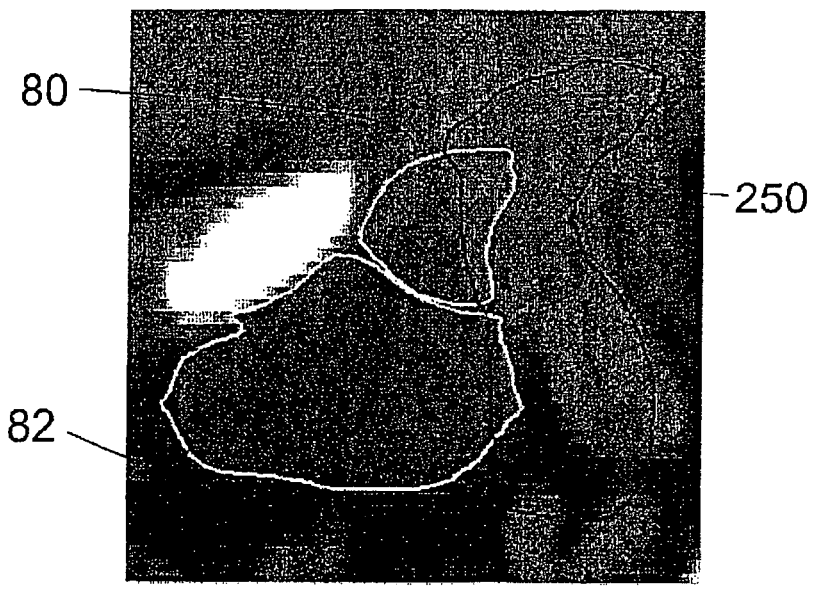
FIGS. 8A and 8B show results of an example contouring of a rectum with and without using the overlap prevention technique of FIG. 7.
Figure 8B:
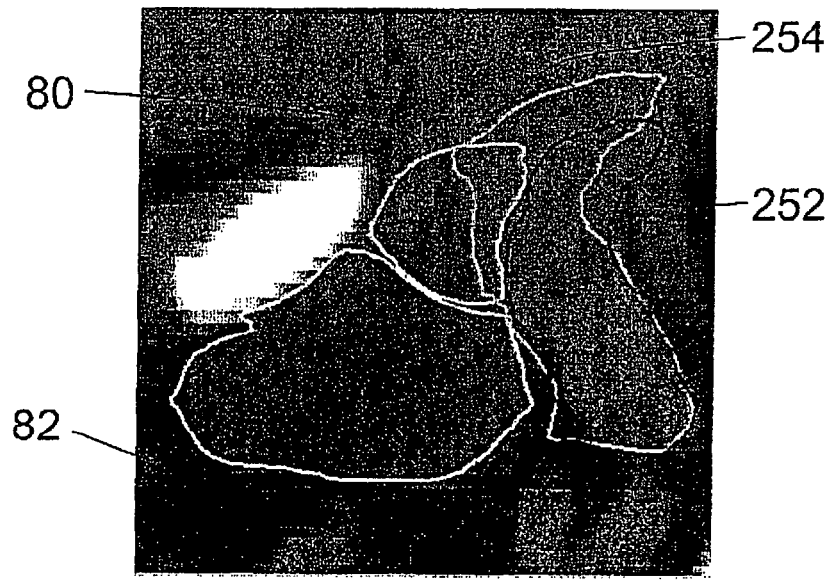

With reference to FIGS. 8A and 8B, example segmentation results achieved using the automated contours optimization process flow illustrated in FIG. 7 are illustrated. The image in FIG. 8A is the same as the image of FIG. 3A, and includes the two adjusted meshes or contours 80, 82 corresponding to bladder and prostate organs, whose binary mask was illustrated in FIG. 3B. An initial rectum contour 250 is also shown in FIG. 8A. The optimization process of FIG. 7 was applied to the initial contour 250 to produce a fitted rectum contour 252 shown in FIG. 8B that does not overlap the previously adjusted meshes or contours 80, 82. In contrast, a similar fitting process starting with the initial contour 250, but which did not include the overlap prevention criterion, produced the fitted rectum contour 254 also shown in FIG. 8B. This latter fitted rectum contour 254 strongly overlaps the defined contour 80.

It will be appreciated that the contouring techniques described herein can be used to adapt either two-dimensional or three-dimensional meshes to features of interest in a corresponding two-dimensional or three-dimensional image. Moreover, while the contouring apparatuses and methods described herein are described with reference to computed tomography planning images for a radiotherapy session, the contouring or image segmentation apparatuses and methods described herein can be employed to segment images acquired by substantially any type of imaging modality, such as by a magnetic resonance imaging scanner, a single photon emission computed tomography (SPECT) scanner, a positron emission tomography (PET) scanner, an x-ray system, or so forth. Still further, while the contouring or image segmentation apparatuses and methods described herein are described with reference to application in radiation therapy planning, it will be appreciated that these image segmentation apparatuses and methods can be employed in substantially any application that benefits from segmentation of images.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. An image segmentation method for segmenting a plurality of image features in an image, the segmentation method comprising:
   segmenting the plurality of image features non-simultaneously in succession, the segmenting of each image feature including adapting an initial mesh to boundaries of the image feature, the segmenting of each image feature further including preventing the adapted mesh from overlapping any previously adapted mesh;
   wherein the adapting of the initial mesh to boundaries of the image feature includes iteratively adjusting portions of the mesh using a plurality of adjustment selection criteria and, after each iterative adjustment, (i) identifying any adjusted portions of the mesh that overlap a previously adapted mesh and (ii) repositioning any identified adjusted overlapping portions of the mesh outside of the previously adapted mesh.

2. The segmentation method as set forth in claim 1, further including:
   after segmenting the image feature, displaying the adapted mesh overlaid on the image;
   adjusting the displayed adapted mesh based on user inputs; and
   during the adjusting of the displayed adapted mesh, preventing the adjusting from causing the displayed adapted mesh to overlap any previously adapted mesh.

3. The segmentation method as set forth in claim 1, wherein the mesh is a polygonal mesh, the portions of the mesh are polygonal mesh components, the identified overlapping portion of the mesh is an identified polygonal mesh component, and the repositioning of the identified portion of the mesh outside of the previously adapted mesh includes:
   shifting vertices of the identified polygonal mesh component along a selected direction to a position outside of the previously adapted mesh.

4. An image segmentation apparatus for segmenting a plurality of image features in an image, the segmentation apparatus comprising:
   a computer programmed to segment the plurality of image features non-simultaneously, the segmenting of each image feature including:
      defining a mesh corresponding to the image feature,
      iteratively adapting the defined mesh to the image feature, the iterative adapting being applied to only one defined mesh at any given time, and
      after each iteration of the iterative adapting, (i) determining whether the iteration caused the defined mesh currently being adapted to overlap another defined mesh and (ii) adjusting the defined mesh currently being adapted to remove said determined overlap.

5. The image segmentation apparatus as set forth in claim 4, further comprising:
   a user interface for (i) receiving a user input selecting one of the defined meshes as the defined mesh currently being adapted and (ii) receiving adaptation user inputs, each adaptation user input causing an iteration of the iterative adapting.

6. The image segmentation apparatus as set forth in claim 4, wherein the segmenting of each image feature further comprises:
   generating a binary mask indicating excluded pixels or voxels of the image which are contained by one of the defined meshes other than the defined mesh currently being adapted, the binary mask being used in the determining of whether the iteration caused the defined mesh currently being adapted to overlap another defined mesh.

7. A radiation therapy apparatus comprising:
   a planning imager for acquiring one or more planning images of a radiotherapy subject;
   a segmentation apparatus as set forth in claim 4 for segmenting at least one planning image to produce contours each representative of one of (i) tissue to be treated and (ii) tissue at risk;
   a radiation treatment planner for developing a radiation treatment plan based on the contours; and
   a radiation delivery system for performing radiation therapy on the radiotherapy subject in accordance with the radiation treatment plan.

8. The segmentation method as set forth in claim 1, wherein the image is a medical diagnostic image generated by one of: (i) a computed tomography scanner, (ii) a magnetic resonance imaging scanner, (iii) a single photon emission computed tomography scanner, (iv) a positron emission tomography scanner, and (v) an x-ray system.

9. A radiation therapy method comprising:
   acquiring one or more planning images of a radiotherapy subject;
   contouring anatomical features in the one or more planning images using the image segmentation method set forth in claim 1 to produce contours each representative of one of (i) tissue to be treated and (ii) tissue at risk;
   developing a radiation treatment plan based on the contours; and
   performing radiation therapy on the radiotherapy subject in accordance with the radiation treatment plan.

10. A medical imaging system including a processor programmed to perform the image segmentation method set forth in claim 1.

11. A radiation therapy apparatus comprising:
   a planning imager for acquiring one or more planning images of a radiotherapy subject;
   an image segmentation apparatus as set forth in claim 4 for segmenting at least one planning image to produce contours each representative of one of (i) tissue to be treated and (ii) tissue at risk;
   a radiation treatment planner for developing a radiation treatment plan based on the contours; and
   a radiation delivery system for performing radiation therapy on the radiotherapy subject in accordance with the radiation treatment plan.

* * * * *